United States Patent [19]

Desai et al.

[11] 4,084,053
[45] Apr. 11, 1978

[54] POLYCYCLIC COMPOUNDS

[75] Inventors: Nalin Binduprasad Desai, Bombay, India; Visvanathan Ramanathan, Basel, Switzerland

[73] Assignee: Ciba-Geigy Corporation, Ardsley, N.Y.

[21] Appl. No.: 587,478

[22] Filed: Jun. 16, 1975

[30] Foreign Application Priority Data

Jun. 21, 1974 Switzerland ............... 8540/74

[51] Int. Cl.² ........................................... C07D 487/14
[52] U.S. Cl. ........................... 544/184; 260/256.4 N; 8/54.2; 8/162 R; 260/154; 544/58; 544/112; 544/82
[58] Field of Search ...................... 260/249.5; 544/184

[56] References Cited

U.S. PATENT DOCUMENTS 3,720,671 3/1973 Kaupp et al. ............... 260/249.5

Primary Examiner—John M. Ford

Attorney, Agent, or Firm—Edward McC. Roberts; Prabodh I. Almaula

[57] ABSTRACT

Polycyclic compounds of the general formula I

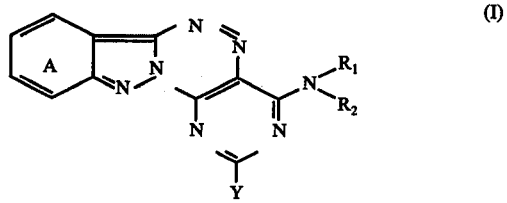

in which the nucleus A can be further substituted, Y is a hydrogen atom or an optionally substituted hydrocarbon radical, and $R_1$ and $R_2$ each denote hydrogen, aryl, aralkyl, cycloalkyl or an aliphatic radical, and $R_1$ and $R_2$ can form a ring containing the amine nitrogen and mixtures thereof with one another. The dyestuffs dye natural and synthetic fibres in fast yellow and orange shades.

16 Claims, No Drawings

POLYCYCLIC COMPOUNDS

The present invention relates to new polycyclic compounds, a process for their manufacture, the use of the new polycyclic compounds for dyeing or printing organic material, especially the use of the polycyclic compounds which are sparingly soluble in water as disperse dyestuffs for dyeing or printing hydrophobic organic fibre material, and, as an industrial product, the material dyed or printed with the new polycyclic compounds.

New, valuable, polycyclic compounds have been found which correspond to the general formula I

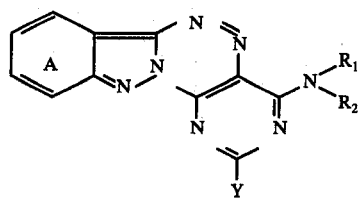

in which the nucleus A can be further substituted, Y can be a hydrogen atom or a hydrocarbon radical, such as, for example, an optionally substituted alkyl or aryl radical, preferably an optionally substituted alkyl or aryl radical, preferably an optionally substituted lower alkyl or phenyl radical, $R_1$ and $R_2$ each denote hydrogen or an aryl, aralkyl, cycloalkyl or aliphatic radical, and $R_1$ and $R_2$ can form a ring containing the amine nitrogen.

These new polycyclic compounds of the general formula I are obtained if the diazonium compound of an amine of the formula II

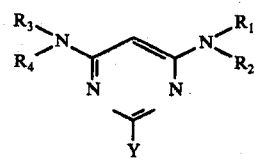

in which the nucleus A has the meaning indicated under formula I, is coupled with a pyrimidine compound of the formula III

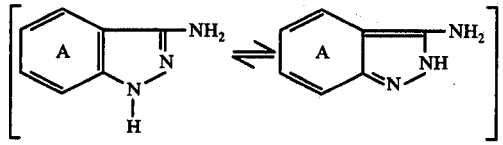

in which $R_3$ and $R_4$ each denote hydrogen, aryl, aralkyl or cycloalkyl radicals or an aliphatic radical, $R_3$ and $R_4$ can form a ring containing the amine nitrogen, and $R_1$, $R_2$ and Y have the meaning indicated under formula I, to form an azo compound of the formula IV

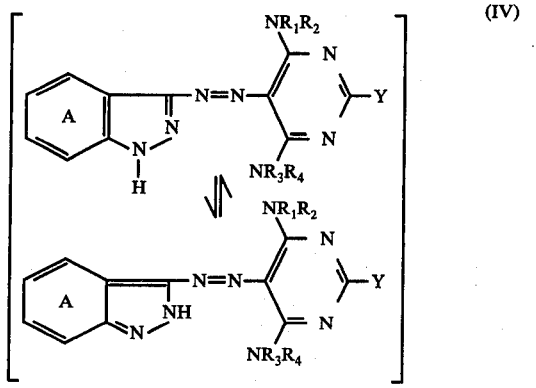

and the coupling product is reacted, with elimination of $HNR_3R_4$ and cyclisation, to form a polycyclic compound of the formula I.

Possible substituents of the nucleus A are particularly: the nitro group, the nitrile group, halogen, optionally sulphonamide groups, lower alkyl groups, lower alkoxy groups, optionally substituted alkylsulphonyl groups such as, for example, hydroxyethylsulphonyl groups or the sulphonic acid group.

Examples of $R_1$, $R_2$, $R_3$ and $R_4$ as hudrocarbon radicals are straight-chain or branched alkyl groups with up to 12, preferably 1 to 6, carbon atoms, cycloalkyl groups, such as the cyclohexyl group, aralkyl groups, especially phenylalkyl groups, such as the benzyl group, and carbocyclic aryl groups, such as phenyl groups or naphthyl groups.

Aliphatic hydrocarbon radicals $R_1$, $R_2$, $R_3$ and $R_4$ can be substituted, for example by hydroxyl or nitrile groups, lower alkoxy groups with preferably 1 to 4 carbon atoms, acyloxy groups, phenoxy groups or halogens, such as chlorine or bromine. The following should be mentioned individually: methyl, ethyl, propyl, butyl, hexyl, β-ethylhexyl, β-hydroxyethyl or β-hydroxypropyl, γ-hydroxypropyl, ω-hydroxyhexyl, β-methoxyethyl, γ-methoxypropyl, β-ethoxyethyl, γ-ethoxypropyl, γ-isopropoxypropyl, γ-butoxypropyl, β-aminoethyl, γ-dimethylaminopropyl, γ-dibutylaminopropyl or ω-aminohexyl and the radicals of the formulae $CH_2CH_2OCH_2CH_2OH$,

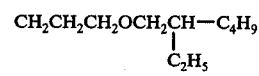

or $CH_2=CH-CH_2$

Examples of possible acyl radicals are fatty acid radicals with up to 5 carbon atoms, such as formyl, acetyl, propionyl or butyryl radicals; alkylcarbamyl radicals with up to 5 carbon atoms, such as methylaminocarbonyl, ethylaminocarbonyl, propylaminocarbonyl or butylaminocarbonyl radicals; alkoxycarbonyl radicals with up to 5 carbon atoms, such as methoxycarbonyl, ethoxycarbonyl, propoxycarbonyl or butoxycarbonyl radicals; phenylcarbamyl radicals or phenoxycarbonyl radicals, or benzoyl, phenoxyacetyl, chloroacetyl or phenylacetyl radicals.

if substituents of the pyrimidine ring possess benzene rings which are further substituted, the latter can also contain the substituents cited for the nucleus A, but especially halogens, such as fluorine, chlorine or bromine, sulphonic acid groups, lower alkyl groups or lower alkoxy groups or phenyl groups.

The polycyclic compounds of the formula I according to the invention in which the nucleus A is optionally substituted by nitro groups or halogens, such as chlorine, and which are free from groups which dissociate in water and confer solubility in water, are valuable as disperse dyestuffs.

If the nitrogen atom present in the dyestuff of the formula IV forms a hetero-ring conjointly with the substituents $R_1$ and $R_2$ and/or $R_3$ and $R_4$, this ring is preferably 5-membered to 6-membered and not aromatic; it can be, for example, the pyrrolidine or piperidine ring, and, if this ring includes a further heteroatom, for example, the morpholine radical or a piperazine ring which is optionally N'-substituted, especially by alkyl or acyl groups, such as the N'-methylpiperazino, N'-ethylpiperazino or N'-acetylpiperazine radical, or a radical of the formula

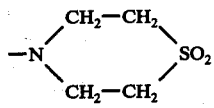

Examples of diazo components of the formula II which are suitable for carrying out the process according to the invention are optionally substituted 3-aminoindazoles, such as 3-aminoindazole, 3-amino-5- or -6-nitroindazole, 3-amino-4- or -5-methylindazole, 3-amino-4,6-dimethylindazole, 3-amino-4- or -5-methoxyindazole, 3-amino-4-,-5- or -6-chloroindazole, 3-amino-5-or -6-bromoindazole, 3-amino-5-methoxy-6-chloroindazole and 3-aminoindazole-5-sulphonic acid.

The coupling components which are to be used in accordance with the invention can be obtained by reacting dihalogenopyrimidines, for example the monochloropyrimidines or dichloropyrimidines of the formulae

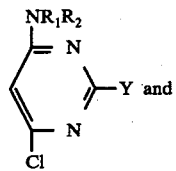 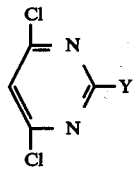

wherein Y has the same meaning as above, with primary or secondary amine.

Examples of suitable monochloropyrimidines or dichloropyrimidines are 2-phenyl-4,6-dichloropyrimidine, 2-(p-chlorophenyl)-4,6-dichloropyrimidine, 2-(p-chlorophenyl)-4-(β-methoxy-ethylamino)-6-chloropyrimidine, 2-phenyl-4-(p-hydroxy-propylamino)-6-chloropyrimidine and 2-(m-nitrophenyl)-4,6-dichloropyrimidine.

The following examples of amines may be mentioned: naphthylamine, aniline and derivatives thereof, such as 1-amino-3-chlorobenzene, 1-amino-4-carbethoxybenzene, 1-amino-2,4-dicyanobenzene, 1-amino-2-methoxy-4-nitrobenzene, 1-amino-2-methanesulphonyl-4-chlorobenzene, methylaminobenzene, ethylaminobenzene and 1-methylamino-3-chlorobenzene, and primary and secondary aliphatic amines, such as methylamine, ethylamine, isopropylamine, decylamine, tert.-butylamine, isoamylamine, n- or i-hexylamine, n- or i-octylamine, 2-ethylbutylamine, 2-ethylhexylamine, cyclohexylamine, β-hydroxyethylamine, β-hydroxypropylamine, γ-hydroxypropylamine, ω-hydroxyhexylamine, β-methoxyethylamine, β-ethoxyethylamine, β-butoxyethylamine, γ-(β'ethylhexoxy)-propylamine, β-(β'-hydroxyethoxy)-ethylamine, γ-ethoxypropylamine, γ-methoxypropylamine, γ-isopropoxypropylamine, γ-amino-α-N-methylaminopropane, γ-amino-α-N-dimethylaminopropane, α-amino-β-diethylaminoethane, β-amino-β-ethyl-α,γ-propanediol, β-amino-β-methylpropanol, N-ethyl-N-(β-hydroxyethyl)-amino, diethanolamine, dimethylamine, diethylamine, dipropylamine, N-methyl-N-(β-hydroxy-ethyl)amine, morpholine, piperidine, piperazine, N-methylpiperazine, pyrrolidine, thiomorpholine-S-dioxide, β-aminoethyl-thiomorpholine-S-dioxide, N-(γ-aminopropyl)-pyrrolidone, chloroethylamine, chlorobutylamine or benzylamine.

Amines of the formulae (lower alkyl)$_2$N-lower alkylene-NH$_2$ and (lower alkyl)$_2$N-phenylene-NH$_2$ are particularly valuable for the manufacture of quaternised dyestuffs.

Halogenoalkylamino groups which are already introduced can be reacted subsequently with tertiary amines, such as pyridine and N,N-dimethylhydrazine.

The starting materials are preferably coupling components of the formula

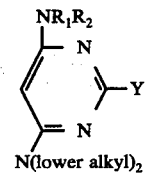

wherein Y is a lower alkyl radical or a phenyl radical and $R_1$ and $R_2$ denote the same as above.

Examples of the last-mentioned coupling components are:

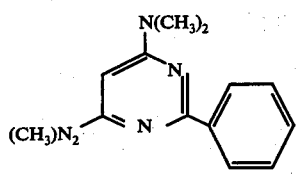 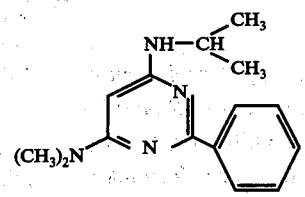

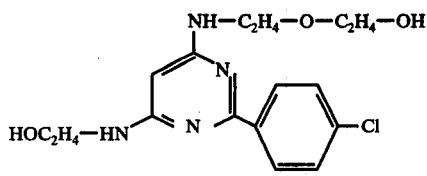
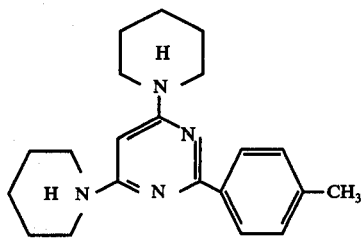

-continued

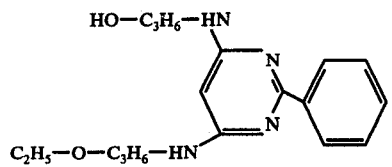
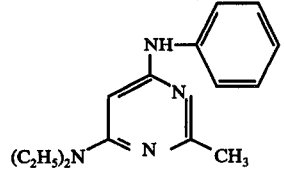
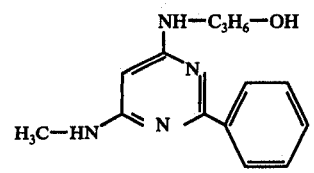
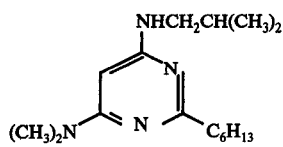
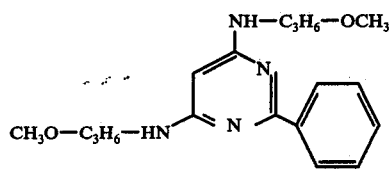
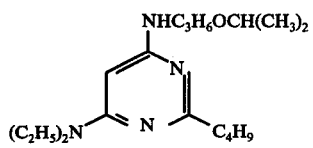
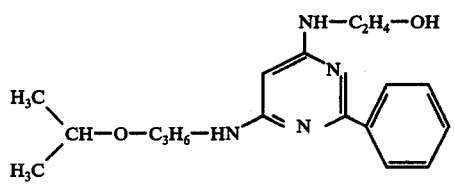
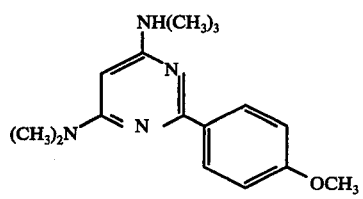
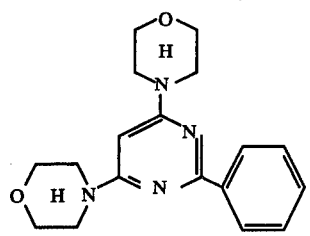

Preferred representatives are the coupling components of the formula

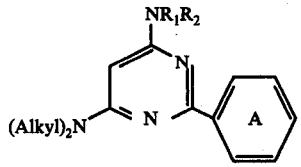

wherein the ring A' can carry alkyl groups, a halogen atom, nitro groups, alkoxy groups, aminocarbonyl groups, alkoxycarbonyl groups and/or alkylcarbonyl groups.

Instead of a unitary diazo component, it is also possible to use a mixture of two or more of the diazo components according to the invention.

The coupling of the diazonium compound of an amine of the formula II with the pyrimidine coupling component of the formula III is carried out according to customary methods, preferably in an acid, aqueous or organic-aqueous medium, particularly at a pH value of 2 to 6. In order to isolate the coupling product, the acid, in the case of mineral acid coupling, is gradually neutralised, for example with alkali metal salts of lower fatty acids, such as sodium acetate.

The reaction of the coupling product (azo compound) of the formula IV, with the elimination of $HNR_3R_4$ and cyclisation to give a polycyclic compound of the formula I, can be carried out, for example, by heating the coupling product in inert, organic solvents which boil above 100° C, but, where appropriate, can be suitably carried out by heating in an acid, aqueous or aqueous-organic medium.

The coupling product can be directly reacted further by heating the acid coupling mixture, without isolation. In some cases it is expedient to isolate the coupling product beforehand. The isolated product is then advantageously introduced into an organic solvent or into an acid, aqueous, organic-aqueous or organic solution and cyclised to form a polycyclic compound of the formula I by subsequent heating.

The reaction temperature can be between 50° and 150° C, depending on the nature of the reaction medium.

Suitable organic solvents are those which are miscible with water, especially lower alcohols, such as methanol, ethanol or isopropanol, ethylene glycol monomethyl ether or ethylene glycol monoethyl ether, cyclic ethers, such as dioxane or tetrahydrofurane, amides of lower fatty acids, such as dimethylformamide, or lower aliphatic sulphoxides, such as dimethylsulphoxide.

Examples of suitable organic and inorganic acids are lower fatty acids, such as acetic acid or formic acid, hydrochloric acid, sulphuric acid, phosphoric acid or nitric acid.

The reaction can also be carried out by heating the coupling product, after isolation, to 100° – 150° C in a high-boiling organic solvent. Examples of suitable high-boiling organic solvents are optionally halogenated or optionally nitrated aromatic hydrocarbons, such as toluene, xylenes, chlorobenzene, o-dichlorobenzene or nitrobenzene, or higher alcohols, such as amyl alcohol, cyclohexanol or benzyl alcohol.

Those of the new compounds which contain a quaternised amino group can be obtained by quaternising the corresponding dyestuffs which contain a non-quaternised amino group, by treatment with alkylating agents.

Examples of such alkylating or quaternising agents which can be used are: esters of strong mineral acids or of organic sulphonic acids, for example dimethyl sulphate or diethyl sulphate, alkyl halides, for example methylchloride, methyl bromide or methyl iodide, aralkyl halides, for example benzylchloride, esters of low molecular alkanesulphonic acids, such as, for example, methyl esters of methanesulphonic acid, ethanesulphonic acid or butanesulphonic acid, and esters of benzenesulphonic acids which can additionally contain substituents, for example the methyl, ethyl, propyl or butyl esters of benzenesulphonic acid; suitable quaternising agents are also α,β-unsaturated compounds, such as methacrylic acid amide, vinyl ethyl ketone, vinyl ethyl ether and above all acrylic acid amide, these compounds being used conjointly with an acid, as a proton donor, such as undiluted acetic acid, sulphuric acid or hydrogen chloride. Other quaternising agents are oxonium salts, such as, for example, triethyleneoxonium fluoborate.

The alkylation is appropriately carried out by heating in an inert organic solvent, for example hydrocarbons, such as benzene, toluene or xylene, halogenated hydrocarbons, such as carbon tetrachloride, tetrachloroethane, chlorobenzene or o-dichlorobenzene, or nitrohydrocarbons, such as nitromethane, nitrobenzene or nitronaphthalene. Acid anhydrides, acid amides or nitriles, such as acetic anhydride, dimethylformamide or acetonitrile or even dimethylsulphoxide can also be used as solvents in the alkylation. Instead of a solvent, it is also possible to use a large excess of the alkylating agent. In this case, however, care must be taken that the mixture does not heat up excessively, since the reaction is strongly exothermic. Nevertheless, in most cases, particularly in the presence of organic solvents, it is necessary to heat the reaction mixture externally in order to start the reaction. In particular cases the alkylation can also be carried out in an aqueous medium or by using an alcohol, possibly in the presence of small quantities of potassium iodide.

If necessary, the salts can be suitably purified by dissolving in water, it being possible to filter off any unreacted starting dyestuff as an insoluble residue. The dyestuff can be precipitated again from the aqueous solution by the addition of water-soluble salts, for example sodium chloride.

The dyestuffs which are not quaternised and are free from sulpho groups are, as a rule, insoluble in water.

Typical representatives of quaternised dyestuffs are, for example, those of the formulae

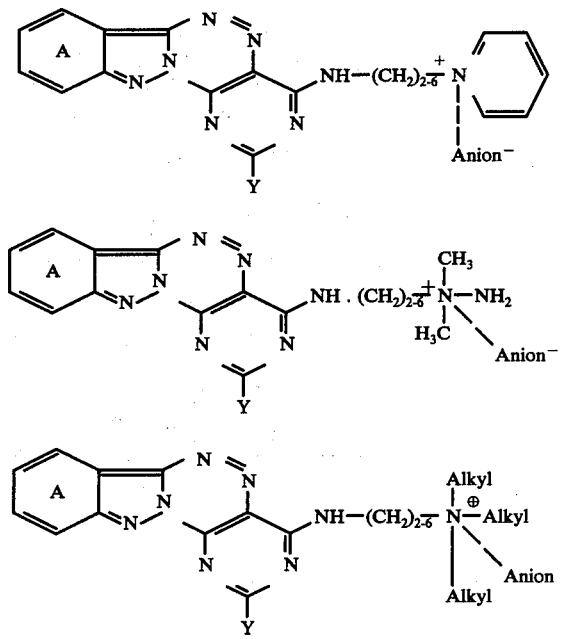

wherein A and Y denote the same as above.

In most cases, the new polycyclic compounds of the formula I crystallise out from the reaction mixture. They are isolated by filtration or by removal of the organic solvent by distillation or steam distillation and they can, if necessary, be purified by recrystallisation, for example from dimethylformamide, ethanol, isopropanol or chlorobenzene. Polycyclic compounds of the formula I, according to the invention, which contain no groups, such as sulphonic acid groups, which dissociate in water in an acid manner, are sparingly soluble or insoluble in water. On the other hand, they are soluble in organic solvents, such as dioxane, ethylene glycol monomethyl ether, dimethylformamide, dimethylsulphoxide, chlorobenzene, o-dichlorobenzene, ethanol, isopropanol and chloroform, the organic solutions of these new polycyclic compounds exhibiting a yellow-green fluorescence in ultraviolet light and in daylight.

The new compounds, mixtures thereof with one another and mixtures thereof with other azo dyestuffs are excellently suitable for dyeing and printing leather, wool, silk and above all synthetic fibres, such as, for example, acrylic or acrylonitrile fibres, polyacrylonitrile fibres and copolymers of acrylonitrile and other vinyl compounds, such as acrylic esters, arylamides, vinylpyridinne, vinyl chloride or vinylidene chloride, copolymers of dicyanoethylene and vinyl acetate, and of acrylonitrile block copolymers, fibres composed of polyurethanes, polyolefines, such as polypropylene modified by a base, polypropylene modified with nickel or unmodified polypropylene, cellulose triacetate and cellulose 2½-acetate and particularly fibres composed of polyamides, such as nylon 6, nylon 6,6 or nylon 12, and of aromatic polyesters, such as those of terephthalic acid and ethylene glycol or 1,4-dimethylcyclohexane, and copolymers of terephthalic acid and isophthalic acid and ethylene glycol.

The new dyestuffs which are free from sulpho groups and quaternised nitrogen atoms are particularly suitable for dyeing textile material consisting of high molecular organic esters, such as cellulose 2½-acetate or cellulose triacetate, but particularly for dyeing or printing textile material of polymeric esters of aromatic polycarboxylic acids with polyhydric alcohols, above all polyethylene glycol terephthalate or polycyclohexanedimethylol terephthalate or texturised polyester fibres, such as, for example, DIOLEN LOFT® (Vereinigte Glanzstoff-Werke), CRIMPLENE® (ICI), and SCHAPIRA® (Hoechst). The dyestuffs can, however, also be used for dyeing synthetic polyamide fibres, such as polyhexamethylene adipamide, polycaprolactam or polyminoundecanoic acid, and for dyeing polyolefines, especially polypropylene fibres. They belong to the class of the disperse dyestuffs, such as are defined, for example, in the Colour Index.

In addition, depending on the composition, they are suitable for bulk dyeing or pigmenting lacquers, oils and waxes and cellulose derivatives, especially cellulose esters, such as cellulose acetate.

The fibre materials mentioned are preferably dyed from an aqueous dispersion with the azo dyestuffs according to the invention which are sparingly soluble in water. If the dyestuffs according to the invention contain, in the diazo component, hydrophilic groups, such as, for example, one or more hydroxyalkyl, carbonamide or sulphonamide groups, they are best applied from a solvent liquor. It is therefore advisable to disperse finely the examples of dyestuffs which can be used as disperse dyestuffs by grinding with textile auxiliaries, such as, for example, dispersing agents, and, possibly, with further grinding auxiliaries. Dyestuff preparations consisting of the textile auxiliary and the dyestuff are obtained by subsequent drying.

The following examples may be mentioned of dispersing agents of the non-ionic group which can be used with advantage: addition products of 8 mols of ethylene oxide to 1 mol of p-tert.-octylphenol, of 15 or 16 mols of ethylene oxide to castor oil, and of 20 mols of ethylene oxide to the alcohol $C_{16}H_{33}OH$, ethylene oxide addition products with di[α-phenylethyl]-phenols, polyethylene oxide tert.-dodecyl-thioethers, polyamine polyglycol ethers or addition products of 15 or 30 mols of ethylene oxide to 1 mol of the amine $C_{12}H_{25}NH_2$ or $C_{18}H_{37}NH_2$.

The following anionic dispersing agents may be mentioned: sulphuric acid esters of alcohols of the aliphatic series with 8 to 20 carbon atoms, of the ethylene oxide adducts of the corresponding fatty acid amides, or of alkylated phenols with 8 to 12 carbon atoms in the alkyl radical; sulphonic acid esters having alkyl radicals with 8 to 20 carbon atoms; sulphation products of unsaturated fats and oils; phosphoric acid esters having alkyl radicals with 8 to 20 carbon atoms; fatty acid soaps and also alkylarylsulphonates, condensation products of formaldehyde with naphthalenesulphonic acid and lingninsulphonates.

Suitable cationic dispersing agents are quaternary ammonium compounds containing alkyl or aralkyl radicals with 8 to 20 carbon atoms.

In addition to the dispersing agents, the dyestuff preparations can also contain organic solvents, especially solvents which boil above 100° C and which are preferably miscible with water; such as monoalkyl glycol ethers and dialkyl glycol ethers, dioxane, dimethylformamide or dimethylacetamide, tetramethylenesulphone or dimethylsulphoxide. Dyestuff, dispersing agent and solvent can advantageously be ground with one another.

The polyester fibres are dyed from an aqueous dispersion with the dyestuffs according to the invention which are sparingly soluble in water, according to processes which are customary for polyester materials. Polyesters of aromatic polycarboxylic acids with polyhydric alcohols are preferably dyed at temperatures of above 100° C and under pressure. The dyeing can, however, also be carried out at the boiling point of the dye bath in the presence of dyestuff carriers, for example alkali metal phenylphenolates, polychlorobenzene compounds or similar auxiliaries, or can be carried out by the padding process and subsequent hot after-treatment, for example thermofixing at 180° to 210° C. Cellulose 2½-acetate fibres are preferably dyed at temperatures of 80° to 85° C, while cellulose triacetate fibres and synethetic polyamide fibre material are dyed advantageously at the boiling point of the dye bath. When the lastmenioned kinds of fibres are dyed, the use of dyestuff carriers is superfluous.

The dyeings obtained according to the present process can be subjected to an after-treatment, for example by heating with an aqueous solution of a non-ionic detergent.

The textile materials mentioned are also printed according to the customary methods, for example by printing the goods with the printing paste containing, in addition to the dyestuff and the dyeing accelerator, thickeners and customary additives, such as, for example, urea, and subsequently fixing the dyestuff by steaming for 15 minutes at 100° to 130° C.

It is furthermore possible, for example, to dye snythetic fibres, such as polyesters and polyamides, in organic solvent liquors, such as a mixture of perchloroethylene and dimethylformamide or methanol, or in perchloroethylene alone, or perchloroethylene-water emulsions.

The polycyclic compounds of the formula I which can be used as disperse dyestuffs are very well absorbed on the abovementioned hydrophobic organic fibre material, particularly on polyethylene glycol terephthalate fibres and, on this fibre material, they yield pure, full, greenish-tinged yellow, yellow and reddish-tinged yellow dyeings with a high brilliance and fluorescence. In addition, the dyeings are very fast to washing, fulling, rubbing, perspiration, solvents, decatising, light and sublimation.

Polycyclic compounds of the formula I according to the invention are particularly distinguished by high tinctorial strength and brilliance associated with very good fastness to light and sublimation of dyeings thereof on polyethylene glycol terephthalate fibres and, in addition, have good levelling properties on texturised polyester fibres.

Those new compounds of the formula I which contain groups, for example sulphonic acid groups, which dissociate in water in an acid manner, can be used for dyeing or printing, from an acid to neutral bath, natural polyamide fibres, such as wool, or synthetic polyamide fibres, such as nylon, as well as texturised polyamide fibres, such as Banlon.

The quaternised dyestuffs or dyestuff salts, obtained in accordance with the invention, having an optionally quaternised amino group, a hydrazino-etherified hydoxylamino group or a heterocyclic group containing nitrogen, are suitable for dyeing and printing the most diverse fully synthetic fibres, such as, for example, polyvinylchloride, polyamide or polyurethane fibres, and also fibres of polyesters of aromatic dicarboxylic acids, such as, for example, acid modified polyethylene terephthalate fibres, but especially polyacrylonitrile fibre materials or fibres of polyvinylidene cyanides.

By polyacrylonitrile fibres are understood above all polymers containing more than 80%, for example 80 to 95%, of acrylonitrile; they contain, besides, 5 to 20% of vinyl acetate, vinylpyridine, vinyl chloride, vinylidene chloride, acrylic acid, acrylic acid esters, methacrylic acid, methacrylic acid esters and the like.

In general, the quaternised dyestuffs are not very sensitive to electrolytes and are soluble in water or polar solvents. Dyeing with the quaternised, water-soluble dyestuffs is generally carried out in an aqueous, neutral or acid medium, at the boil under atmospheric pressure or in a closed vessel under elevated temperature and elevated pressure.

They can also be applied to the fibre materials by printing. For this purpose use is made, for example, of a printing paste containing the dyestuff in addition to the auxiliaries which are customary in printing. They are also suitable for the bulk dyeing of polymerisation products of acrylonitrile, and also of other plastic, optionally dissolved compositions, in shades which are fast to light and washing, and also for dyeing oil paints or lacquers, or, finally, also for dyeing cellulose, regenerated cellulose, paper and especially mordanted cotton.

The new dyestuffs can also be used in the form of their transiently water-soluble derivatives for dyeing polyester fibres. Such transiently water-soluble dyestuffs are obtained, for example, by esterifying the dyestuffs according to the invention with chloroacetic acid and subsequently treating the resultant esters with a tertiary amine to replace the chlorine atom.

The new dyestuffs are also suitable for dyeing cellulose fibres which swell in water using organic swelling agents, such as ethylene glycol, diethylene glycol or diethylene glycol monomethyl ether, at temperatures of 150° to 200° C. Polyester/cotton blends can also be dyed in this way.

In the following example, unless otherwise stated, parts denote parts by weight and percentages denote percentages by weight.

EXAMPLE 1

A mixture of 22.5 parts of 2-phenyl-4,6-dichloropyrimidine, 30 parts of dimethylamine and 100 parts of ethyl alcohol is heated at 110–120° C in an autoclave for 12 hours. On cooling, the compound of the formula

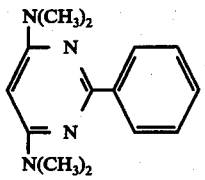

is precipitated in straw-yellow needles (melting point 124–126° C).

17.8 parts of 3-amino-5nitroindazole are added slowly to a solution of 6.9 parts of sodium nitrite in 180 parts of concentrated sulphuric acid. The mixture is stirred for 30 minutes at room temperature and is then poured onto 500 parts of ice. After removing, by means of sulphamic acid, any excess nitrous acid which may be present, the solution is filtered and the filtrate is added at 0–5° C to a solution of 24.2 parts of 2-phenyl-4,6-bis(dimethylamino)-pyrimidine in 200 parts of a mixture of acetic acid and propionic acid (mixing ratio 5:1). The mixture is stirred at 0–5° C for about 2 to 3 hours, until the coupling is complete, is diluted with 200 parts of water and is then heated at 95 to 100° C for 1.5 to 2 hours. After cooling, the yellow-brown precipitate which has formed is filtered off, washed and dried. It consists of the dyestuff of the formula

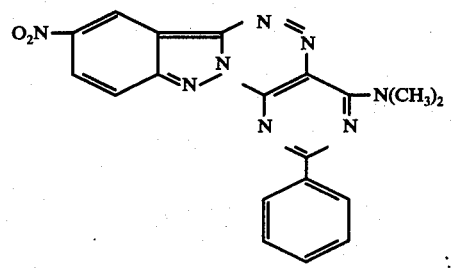

which exhibits a strong green fluorescence in organic solvents and which dyes polyester fibres from an aqueous dispersion in brilliant yellow shades with good fastness to light and good fastness to sublimation.

Dyeing instruction 1 part of the dyestuff obtained in accordance with Example 1 is ground wet with 2 parts of a 50% strength aqueous solution of the sodium salt of dinaphthylmethanedisulphonic acid and is dried.

This dyestuff preparation is stirred with 40 parts of a 10% strength aqueous solution of the sodium salt of N-benzyl-μ-heptadecylbenzimidazoledisulphonic acid and 4 parts of a 40% strength acetic acid solution are added. A dye bath of 4,000 parts is prepared from this by dilution with water.

100 parts of a purified polyester fibre material are introduced into this bath at 50° C, the temperature is raised to 120°–130° C over the course of half an hour and dyeing is carried out at this temperature for one hour in a closed vessel.

The material is then well rinsed. A full, yellow dyeing is obtained with excellent fastness to light and sublimation.

EXAMPLE 2

(a) A mixture of 22.5 parts of 2-phenyl-4,6-dichloropyrimidine, 10 parts of dimethylamine (as 30% alcoholic solution) and 100 parts of alcohol is refluxed for 1 hour and the solvent is then removed completely by distillation under reduced pressure. The straw-coloured crystalline residue is taken up in water, filtered, washed with water and dried. The monodimethylamino derivative crystallizes

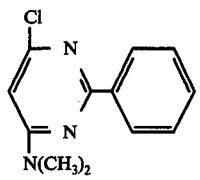

from cyclohexane in stout, colourless needles, m.p. 94°

(b) A mixture of 23.3 parts of the above monodimethylamino compound, 18 parts of isopropylamine and 200 parts of alcohol is heated in an autoclave at 130–40° for 12 hours. The content of the autoclave is then cooled and the separated colourless, crystalline product

is filtered, washed with water and dried.

(c) 16.8 Parts of 3-amino-6chloroindazole are gradually added to a solution of 6.9 parts of sodium nitrite in 180 parts of concentrated sulphuric acid at room temperature. The clear solution is stirred at room temperature for 30 minutes and then poured over 500 parts of crushed ice. After destroying the excess of nitrous acid, if present, with sulphamic acid, the diazo solution is filtered from small amount of suspended impurities and the clear filtrate is run into a solution of 25.6 parts of 2-phenyl-4-isopropylamino-6-dimethylaminopyrimidine described in para (b) above in 200 parts of a 5:1 mixture of acetic acid and propionic acid at 0–5°. The mixture is stirred at this temperature unitl the coupling is complete (2–3 hours), is diluted with 200 parts of water and then heated to 95–100° for 2 hours. The yellow brown precipitate is filtered hot, washed with water and dried. The dyestuff

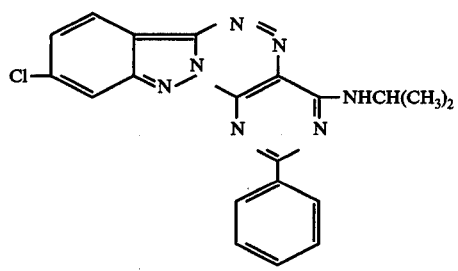

gives a bright yellow shade with excellent fastness properties on polyester.

EXAMPLE 3

(a) A mixture of 16.3 parts of 2-methyl-4,6-dichloropyrimidine, 10 parts of dimethylamine (as 30% alcoholic solution) and 100 parts of alcohol is refluxed for 1 hour. After completely removing the solvent by distillation under reduced pressure, the residue is stirred with 100–200 parts of ether.

The insoluble dimethylamine hydrochloride is filtered off and the monodimethylamino derivative:

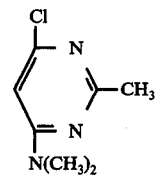

is recovered from ether filtrate as colourless crystals, m.p. 68°–70°.

(b) A mixture of 17.1 parts of above monodimethylamino derivative, 18.0 parts of monoethanolamine and 100 parts of alcohol is heated in autoclave at 130°–40° for 12 hours. After cooling, the solvent is completely removed and the residue of the pale, yellow, viscous oil is used for the next step without any further purification.

(c) 16.8 parts of 3-amino-6-chloroindazole are diazotised as described in para (c) of Example 2 and the clear diazo solution is run into the solution of the crude product described in para (b) above (containing 19.6 parts of

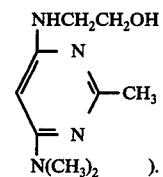

in 200 parts of 5:1 mixed acetic acid propionic acid at 0°–5°. After stirring at 0°–5° for 2–3 hours, the mixture is heated at 95° to 100° for 1.5 to 2 hours. The separated yellow-brown precipitate of the dyestuff:

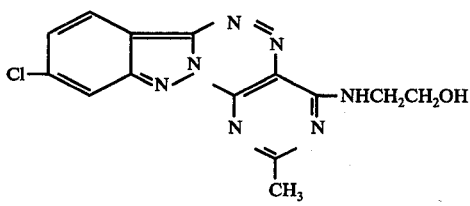

is filtered, washed and dried. The dyestuff is applied to polyester from aqueous dispersion and the resulting bright yellow dyeing exhibits excellent fastness to light and sublimation.

EXAMPLE 4

10.2 parts of acetic anhydride are added to a boiling solution of 16.0 parts of the dyestuff, described in para (c) of Example 3, in 80 parts of pyridine and the mixture is further refluxed for 10 minutes. On cooling the dyestuff of formula:

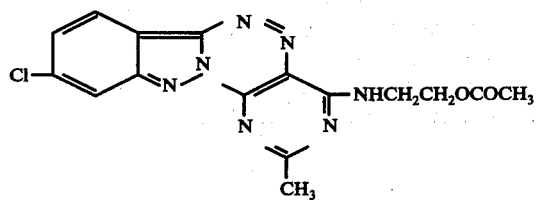

separates as orange yellow crystals. It also dyes polyester in a pure yellow tone with excellent fastness properties.

EXAMPLE 5

(a) A mixture of 14.9 parts of 4,6-dichloropyrimidine, 10 parts of dimethylamine and 100 parts of alcohol is refluxed for 1 hour. After removing the solvent, the crystalline residue is stirred with 100 parts of ether. The insoluble hydrochloride of dimethylamine is filtered off and the product

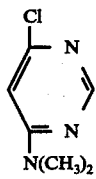

is recovered from ether filtrate; it crystallizes from cyclohexane in stout, colourless needles, m.p. 105°–106°.

(b) A mixture of 15.7 parts of 4-chloro-6-dimethylaminopyrimidine, 33.0 parts of isopropoxylpropylamine and 100 parts of alcohol is heated in an autoclave at 130°–40° for 12 hours. The mixture is cooled and the residual semi-solid mass obtained after the removal of the solvent is extracted with hot petroleum ether. The petroleum ether extract, on cooling, gives the product:

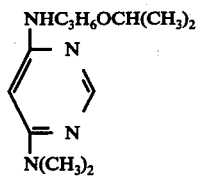

as colourless plates, m.p. 69°–71°.

(c) 16.8 parts of 3-amino-6-chloroindazole are diazotised as described in para (c) of Example 2 and the clear diazo solution is run into the solution of 23.8 parts of the coupling component, described in (b) above, in 200 parts of mixed acetic acid propionic acid (mixing ratio 5:1) at 0°–5°. After stirring at 0°–5° for 2 to 3 hours, it is diluted with 200 parts of water and heated at 95° to 100° for another 2 hours. The precipitate of yellow dyestuff:

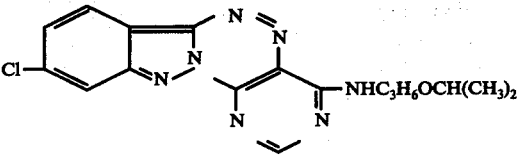

is filtered, washed and dried. It dyes polyester a deep yellow shade of excellent fastness to light and sublimation.

EXAMPLE 6

(a) A mixture of 22.5 parts of 2-phenyl-4,6-dichloropyrimidine, 40.0 parts of morpholine and 200 parts of alcohol is heated in a closed vessel at 100° for 12 hours. On cooling the reaction mixture, the product:

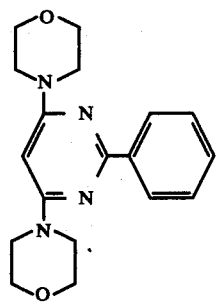

separates as thin, colourless needles, m.p. 185°–87°. It is filtered, washed with water and dried.

(b) 16.3 Parts of 3-amino-5-methoxyindazole are gradually added to a solution of 6.9 parts of sodium nitrite in 180 parts of concentrated sulphuric acid. The solution is stirred at room temperature for one-half hour and then poured over 500 parts of crushed ice. The resulting diazo solution is filtered from small amount of insoluble impurities after removing any excess of nitrous acid with sulphamic acid. The clear filtrate is gradually run into a solution of 32.6 parts of the intermediate, described in (a) above, in 200 parts of 5:1 acetic acid propionic
acid mixture at 0°–5°. The mixture is stirred at 0°–5° for 3 hours, is diluted with 200 parts of water and gently boiled for 1.5 hours. The yellow precipitate of the dyestuff:

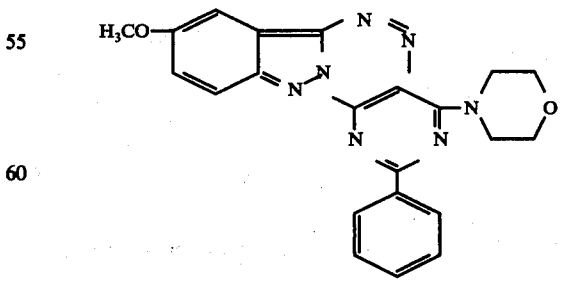

is filtered, washed and dried. It dyes polyester a pure yellow shade with good fastness to light and sublimation.

EXAMPLE 7

(a) A mixture of 22.5 parts of 2-phenyl-4,6-dichloropyrimidine, 40.0 parts of piperidine and 200 parts of alcohol is heated in an autoclave at 100° for 12 hours. On cooling the reaction mixture, the product:

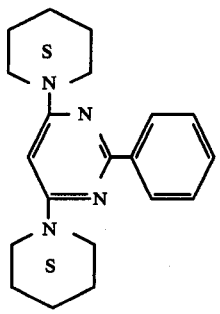

separates as stout, colourless needles, m.p. 180°–182°. It is filtered, washed with water and dried.

(b) 24.0 Parts of N,N-dimethyl-5-(3'-aminoindazolyl) sulphone amide are stirred with a solution of 6.9 parts of sodium nitrite in 180 parts of concentrated sulphuric acid at room temperature for 30 minutes. The mixture is then poured over 500 parts of crushed ice. The resulting diazo solution is freed from excess nitrous acid, if present, and clarified by filtration. The clear diazo solution is introduced into a solution of 32.2 parts of mixed acetic acid and propionic acid and the coupling and the cyclization steps are carried out in the manner described in previous examples. The yellow dyestuff:

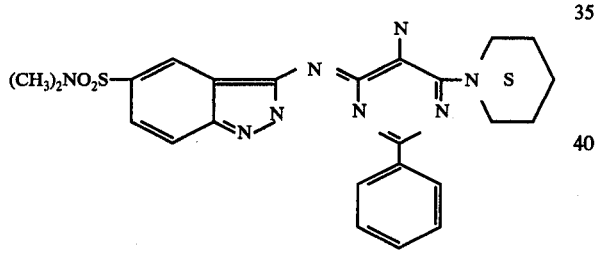

so obtained dyes polyester a bright yellow shade with good fastness properties.

EXAMPLE 8

(a) A mixture of 26.0 parts of 2-(p-chlorophenyl)-4,6-dichloropyrimidine, 20 parts of dimethylamine and 200 parts of alcohol is heated in a closed vessel at 100° for 12 hours. The reaction mixture is then cooled and the separated colourless needles of the product:

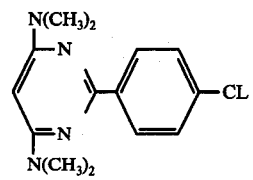

are filtered, washed with water and dried. The product has m.p. 128°–30°.

(b) 22.3 Parts of 3-amino-5,7-dinitroindazole are diazotised and coupled with 27.6 parts of 2-(p-chlorophenyl)-4,6-bisdimethylaminopyrimidine [described in (a)] in usual manner. The coupling mixture is then diluted with 200 parts water and stirred at 95°–100° for 2 hours. The cyclic dye:

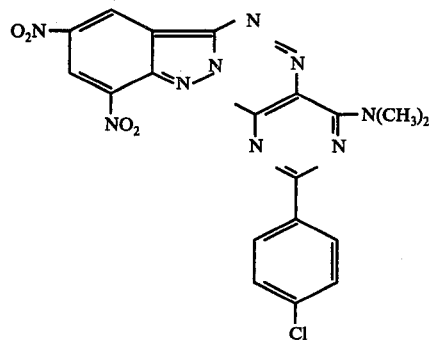

is obtained as orange brown precipitate. It is filtered, washed and dried. On polyester, it gives a reddish yellow shade with good fastness to light and sublimation.

Other examples of the dyestuffs prepared by analogous procedures are given in the following table:

Table 1

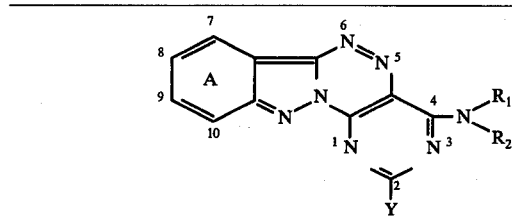

| Ex. | Substituents in ring A | $R_1$ | $R_2$ | Y | Shade on Polyester |
|---|---|---|---|---|---|
| 1 | 8-$NO_2$ | $COCH_3$ | H | Phenyl | greenish-yellow |
| 2 | " | $CH(CH_3)_2$ | " | " | orange |
| 3 | " | $CH_2$ Phenyl | " | " | " |
| 4 | 9-Cl | " | " | " | greenish-yellow |
| 5 | " | $CH_2CH_2OH$ | " | " | " |
| 6 | " | " | " | H | " |
| 7 | " | $C_2H_4OCH_3$ | " | $CH_3$ | " |
| 8 | " | $C_2H_4OCOCH_3$ | " | Phenyl | " |
| 9 | " | $C_3H_6OCH(CH_3)_2$ | " | " | " |

Table 1-continued

![structure with ring A fused to pyrazolo-triazine with substituents R1, R2, Y]

| Ex. | Substituents in ring A | R₁ | R₂ | Y | Shade on Polyester |
|---|---|---|---|---|---|
| 10 | " | Phenyl | " | " | " |
| 11 | " | —C₆H₄—OCH₃ (p-methoxyphenyl) | " | " | " |
| 12 | " | —C₆H₄—Cl (m-chlorophenyl) | " | " | " |
| 13 | 9-Cl | cyclohexyl-S- | H | Phenyl | greenish-yellow |
| 14 | " | CH₃ | CH₃ | p-C₆H₄Cl | " |
| 15 | " | CH(CH₃)₂ | H | " | " |
| 16 | " | CH₃ | CH₃ | p-C₆H₄OCH₃ | " |
| 17 | " | " | " | CH₂Phenyl | " |
| 18 | " | C₃H₆OH | H | Phenyl | " |
| 19 | " | C₃H₆OCOCH₃ | H | " | " |
| 20 | " | C₃H₆OCOPhenyl | " | " | " |
| 21 | " | C₃H₄OCOOC₂H₅ | " | " | " |
| 22 | " | C₃H₆OCH(CH₃)₂ | " | H | " |
| 23 | " | " | " | CH₃ | " |
| 24 | — | CH₃ | CH₃ | Phenyl | yellow |
| 25 | — | CH(CH₃)₂ | H | " | " |
| 26 | — | C₂H₄OCOCH₃ | H | " | " |
| 27 | 9-Br | CH₃ | CH₃ | " | greenish-yellow |
| 28 | " | C₂H₄OCOCH₃ | H | " | " |
| 29 | 8-OCH₃ | " | " | " | " |
| 30 | 8-OC₂H₅ | CH₃ | CH₃ | " | " |
| 31 | 7,9-dimethyl | CH₃ | CH₃ | " | yellow |
| 32 | 8(CH₃)₂NSO₂ | CH₂CH(CH₃)₂ | H | " | " |
| 33 | 8,10-dinitro | CH₃ | CH₃ | H | orange |
| 34 | 8,10-dinitro | C₂H₅ | C₂H₅ | Phenyl | " |
| 35 | 8-CN | CH₃ | CH₃ | " | yellow |
| 36 | — | CH₂CH₂C₆H₅ | H | p-C₆H₄CH₃ | " |
| 37 | 9-Br | C₃H₆OC₂H₅ | H | m-C₆H₄CH₃ | " |

EXAMPLE 9

(a) A mixture of 23.3 parts of 2-phenyl-4-chloro-6-dimethylaminopyrimidine, described in para (a) of Example 2, 20.5 parts of 3-dimethylaminopropylamine and 200 parts of alcohol is treated in an autoclave at 120° for 6 to 8 hours. After cooling, the solvent is completely removed from the reaction mixture and the semi-solid residue, containing 29.9 parts of the product:

is taken up in 200 parts of 5:1 mixture of acetic acid and propionic acid. The solution is cooled to 0°–5° and coupled with 16.8 parts of diazotised 3-amino-6-chloroindazole as described in para (c) of Example 2. After the coupling is complete (2–3 hours), the reaction mixture is diluted with 200 parts of water and heated at 95°–100° for 2 hours. The precipitated yellow dye:

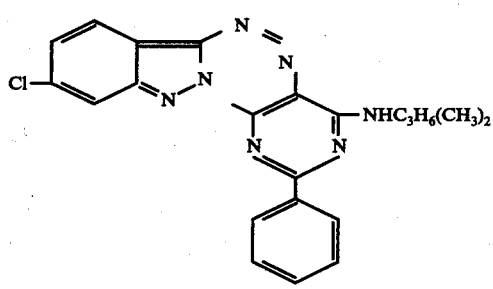

is filtered, washed and dried.

(b) 15.0 Parts of dimethyl sulphate are gradually added to a suspension of 43.2 parts of the above dye in 400 parts of chlorobenzene and the mixture is then refluxed for 1 hour. The solvent is removed from the reaction mixture by steam distillation and the aqueous residue is filtered hot and the clear yellow filtrate is saturated with sodium chloride. On cooling, dyestuff of the formula:

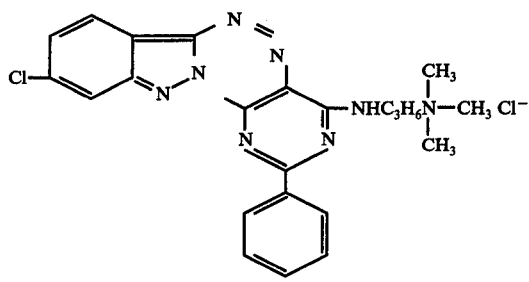

precipitates out. It is filtered and dried. It gives on polyacrylonitrile a pure, bright yellow shade with excellent fastness to light.

Other examples, similarly prepared, are given in Table 2:

coupled with 16.8 parts of diazotised 3-amino-6-chloroindazole and the intermediate dye cyclized in usual manner. The dyestuff:

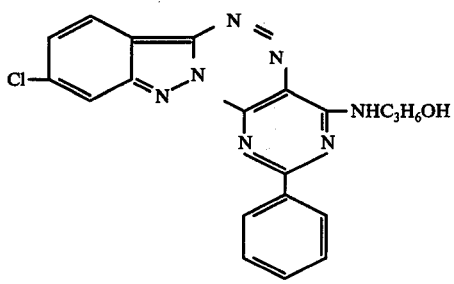

obtained as yellow brown precipitate is filtered, washed and dried.

(b) 17.0 Parts of acid chloride of betain hydrochloride are added to a stirred suspension of 20.0 parts of the above dye (mentioned as Example 26 in the Table 1) in 200 parts of dry chlorobenzene. After the addition, the mixture refluxed with stirring for 1 hour. The yellow brown precipitate formed is separated from chlorobenzene mother liquor by decantation. It is dissolved in 200 parts of boiling water and the yellow brown solution is

Table 2

| Ex. | Substituents in ring A | Y | Z | Quaternizing agent | Shade on Polyacrylonitrile |
|---|---|---|---|---|---|
| 1 | 9-Cl | H | NCH$_3$H$_6$N(CH$_3$)$_2$ | (CH$_3$)$_2$SO$_4$ | yellow |
| 2 | 8-NO$_2$ | Phenyl | | CH$_3$SO$_3$CH$_3$ | orange-yellow |
| 3 | " | CH$_3$ | N N—CH$_3$ | " | " |
| 4 | 9-Cl | Phenyl | NHC$_6$H$_{12}$N(CH$_3$)$_2$ | C$_4$H$_9$SO$_3$CH$_3$ | yellow |
| 5 | ni. | " | NHC$_3$H$_6$N(C$_2$H$_5$)$_2$ | C$_2$H$_5$Cl | " |
| 6 | nil | H | | C$_2$H$_5$Cl | yellow |
| 7 | 9-Br | Phenyl | NHC$_2$H$_4$N(CH$_3$)$_2$ | N N—C$_2$H$_5$ | " |
| 8 | 8,10-dinitro | " | | n-C$_4$H$_9$Cl | " |
| 9 | " | CH$_3$ | " | (CH$_3$)$_2$SO$_4$ | orange |
| 10 | 8-OCH$_3$ | Phenyl | NHC$_3$H$_6$N(CH$_3$)$_2$ | C$_6$H$_4$CH$_2$Br | yellow |
| 11 | 9-Cl | 3-C$_6$H$_4$Cl | " | (CH$_3$)$_2$SO$_4$ | " |
| 12 | " | Phenyl | NHC$_3$H$_6$Cl | | " |
| 13 | " | CH$_3$ | NHC$_3$H$_6$Cl | N(C$_2$H$_5$)$_3$ | " |
| 14 | " | H | NHC$_4$H$_8$Br | N(CH$_3$)$_3$ | " |
| 15 | " | pC$_6$H$_4$CH$_3$ | N(C$_2$H$_5$)C$_2$H$_4$OSO$_2$CH$_3$ | H$_2$NN(CH$_3$)$_2$ | " |
| 16 | " | Phenyl | N(C$_2$H$_5$)C$_2$H$_4$OSO$_2$CH$_3$ | CH$_3$ON(CH$_3$)$_2$ | " |
| 17 | " | " | NHC$_3$H$_6$N(CH$_3$)$_2$ | Propyleneoxide + CH$_3$COOH | " |

EXAMPLE 10

(a) 23.3 Parts of 2-phenyl-4-chloro-6-dimethylaminopyrimidine are heated with 170 parts of 3-aminopropanol in 200 parts of alcohol at 130°–40° for 10 hours. The crude product obtained after the removal of solvent from the cooled reaction mixture, is dissolved in 200 parts of mixed acetic acid and propionic acid and clarified by filtration. The filtrate is heated to 70°-80° and saturated with common salt. On cooling the dyestuff:

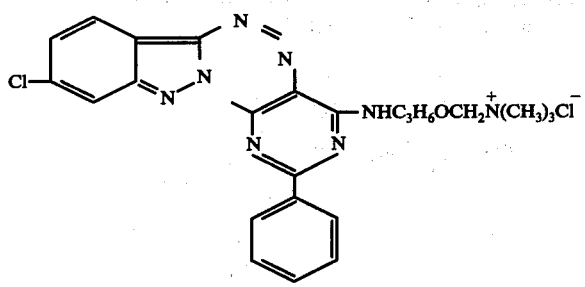

separates as greenish yellow crystalline precipitate. It is filtered, washed and dried.

It dyes both polyester and polyacrylonitrile fibres from aqueous solutions bright yellow shades with excellent fastness to light and sublimation.

EXAMPLE 11

6.6 parts of 3-aminoindazole are dissolved in 200 parts of water and 18 parts by volume of concentrated hydrochloric acid and diazotised at 0° to 5° C with 50 parts by volume of normal sodium nitrite solution. The solution of the diazonium salt is then added dropwise to a solution of 18.5 parts of 2-phenyl-(3'-sulphophenylamino)-6-dimethylamino-pyrimidine in 200 parts of methanol and 15 parts by volume of 30% sodium hydroxide solution. upon termination of the coupling, the reaction mixture is acidified with concentrated hydrochloric acid. The mixture is then heated until the methanol is distilled off, then heated to about 95° C and held at this temperature for 1 hour with stirring. The batch is cooled to room temperature, the precipitate is filtered off and dried to yield a dyestuff of the formula

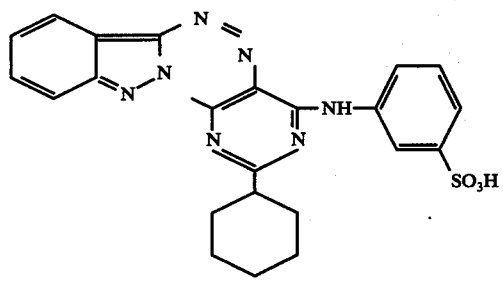

which dyes synthetic polyamide fibres and wool in brilliant, fluorescent yellow shades.

The coupling component is obtained by reaction of 2-phenyl-4-chloro-6-dimethylamino-pyrimidine with metanilic acid.

What is claimed is:

1. A polycyclic compound of the formula

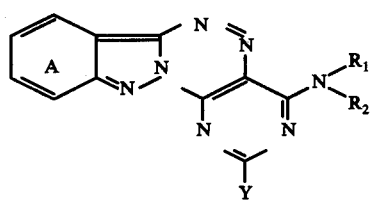

(I)

in which the nucleus A is unsubstituted or substituted by CN, $NO_2$, Cl, Br, $SO_2NH_2$, lower alkyl, lower alkoxy, $C_1$-$C_2$-alkyl-sulphonyl, —$SO_3H$, —$COCH_3$ and —$SO_2$—$N(CH_3)_2$; Y is H, $C_1$-$C_5$-alkyl, phenyl and phenyl substituted by methoxy, methyl, Cl or nitro; and cyclohexyl and benzyl; $R_1$ and $R_2$ are hydrogen, $C_1$-$C_{12}$-alkyl, $C_1$-$C_{12}$-alkyl substituted by OH, CN, $C_1$-$C_4$-alkoxy, Cl, Br, alkanoyloxy of up to 5 carbon atoms, $C_6H_5$—O—, $NH_2$, di($C_1$-$C_4$-alkyl)amino, $CH_2$=CH—$CH_2$—, benzoyloxy, —$(CH_2)_3$—N—$(CH_3)_3$Cl, —$(CH_2)_3$—N—$(CH_3)_3$ $SO_4$, —$(CH_2)_3$—N—$(C_2H_5)_3$ Cl, $C_1$-$C_4$-alkyl-aminocarbonyloxy, $C_1$-$C_4$-alkoxycarbonyloxy, phenoxyacetoxy, phenoxycarbonyloxy, phenylaminocarbonyloxy, chloroacetyl and phenylacetyl; phenyl or phenyl substituted by Br, Cl, —$SO_3H$; and $R_1$ and $R_2$ together are —$CH_2CH_2$—O—$CH_2CH_2$—, —$CH_2CH_2CH_2CH_2$—, —$CH_2CH_2CH_2CH_2CH_2$—, —$CH_2CH_2$—$SO_2$—$CH_2CH_2$—, —$CH_2$—$CH_2$—N—$CH_2$—$CH_2$—$CH_2$—$CH_2$—N—$CH_2CH_2$—,
　　　　　　|　　　　　　　　　　　　　|
　　　　　　$CH_3$　　　　　　　　　　$C_2H_5$ or —$CH_2CH_2$—N($COCH_3$)—$CH_2CH_2$—.

2. A polycyclic compound of claim 1, wherein nucleus A is substituted by CN, $NO_2$, Cl, Br, $SO_2NH_2$, lower alkyl, lower alkoxy, $C_1$-$C_2$-alkylsulphonyl, —$SO_3H$, —$COCH_3$ and —$SO_2$—$N(CH_3)_2$.

3. A polycyclic compound of claim 1, wherein Y is H, $C_1$-$C_5$-alkyl, phenyl and phenyl substituted by methoxy, methyl, Cl or nitro; and cyclohexyl and benzyl.

4. A polycyclic compound of claim 1, wherein Y is phenyl and phenyl substituted by methoxy, methyl, Cl or nitro.

5. A polycyclic compound of claim 1, wherein Y is cyclohexyl or benzyl.

6. A polycyclic compound of claim 1, wherein $R_1$ and $R_2$ are hydrogen, $C_1$-$C_{12}$-alkyl, $C_1$-$C_{12}$-alkyl substituted by OH, CN, $C_1$-$C_4$-alkoxy, Cl, Br, alkanoyloxy of up to five carbon atoms, $C_6H_5$—O—, $NH_2$, di($C_1$-$C_4$-alkyl)amino, $CH_2$=CH—$CH_2$—, benzoyloxy, —$(CH_2)_3$—N—$(CH_3)_3$Cl, —$(CH_2)_3$—N—$(CH_3)_3$ $SO_4$, —$(CH_2)_3$—N—$(C_2H_5)_3$ Cl, $C_1$-$C_4$-alkylaminocarbonyloxy, $C_1$-$C_4$-alkoxycarbonyloxy, phenoxyacetoxy, phenoxycarbonyloxy, phenylaminocarbonyloxy, chloroacetyl and phenylacetyl; phenyl or phenyl substituted by Br, Cl, —$SO_3H$; and $R_1$ and $R_2$ together are —$CH_2CH_2$—O—$CH_2CH_2$—, —$CH_2CH_2CH_2CH_2$—, —$CH_2CH_2CH_2CH_2CH_2$—, —$CH_2CH_2$—$SO_2CH_2CH_2$—, —$CH_2CH_2$—$NCH_3$—$CH_2CH_2$, —$CH_2CH_2$—$NC_2H_5$—$CH_2CH_2$— or —$CH_2CH_2$—$NCOCH_3$—$CH_2CH_2$.

7. A polycyclic compound of claim 1, wherein $R_1$ and $R_2$ together are —$CH_2CH_2$—O—$CH_2CH_2$—, —$CH_2CH_2CH_2CH_2$—, —$CH_2CH_2CH_2CH_2CH_2$—, —$CH_2CH_2$—$SO_2$—$CH_2CH_2$—, —$CH_2CH_2$—$NCH_3$—$CH_2CH_2$—, —$CH_2CH_2$—$NC_2H_5$—$CH_2CH_2$— or —$CH_2CH_2NCOCH_3$—$CH_2CH_2$—.

8. A polycyclic compound of claim 1, wherein at least one of the radicals $R_1$ or $R_2$ contains a sulphonic acid group.

9. A polycyclic compound of claim 1, wherein nucleus A is substituted by at least one sulphonic acid group.

10. A polycyclic compound of claim 1, wherein at least one of the radicals $R_1$ or $R_2$ contains a quaternary nitrogen atom.

11. A polycyclic compound of claim 10, of the formula

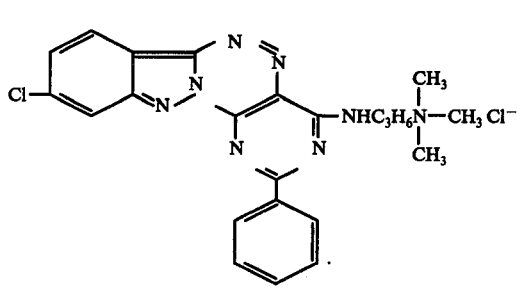
12. A polycyclic compound of claim 1, which is free from acid or basic groups which confer solubility in water.
13. A polycyclic compound of claim 1, of the formula
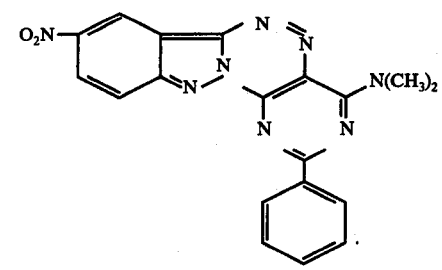
14. A polycyclic compound of claim 1, of the formula
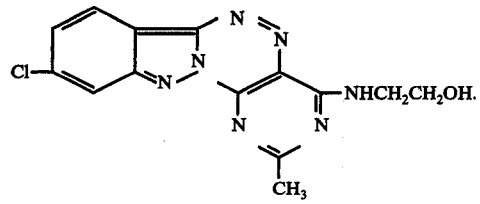
15. A polycyclic compound of claim 1, of the formula
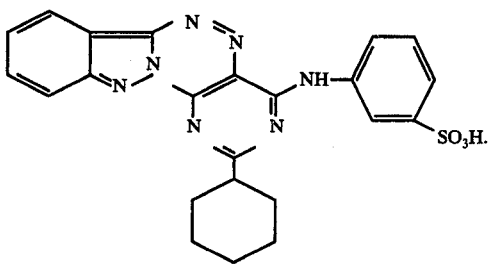
16. A polycyclic compound of claim 1, of the formula
* * * * *